(12) United States Patent
Gabriel

(10) Patent No.: US 6,544,234 B1
(45) Date of Patent: Apr. 8, 2003

(54) INJECTION DEVICE

(75) Inventor: Jochen Gabriel, Stuttgart (DE)

(73) Assignee: B D Medico S.A.R.L., Mies (CH)

( * ) Notice: Subject to any disclaimer, the term of this patent is extended or adjusted under 35 U.S.C. 154(b) by 0 days.

(21) Appl. No.: 09/582,767

(22) PCT Filed: Aug. 7, 1998

(86) PCT No.: PCT/EP98/05015

§ 371 (c)(1),
(2), (4) Date: Jun. 29, 2000

(87) PCT Pub. No.: WO99/37343

PCT Pub. Date: Jul. 29, 1999

(30) Foreign Application Priority Data

Jan. 24, 1998 (DE) ..................................... 298 01 168 U

(51) Int. Cl.⁷ ................................................. A61M 5/00
(52) U.S. Cl. ........................ 604/207; 604/198; 604/218; 604/246; 604/134
(58) Field of Search ................................. 604/110, 192, 604/197, 198, 207, 208, 210, 218, 246, 134–139

(56) References Cited

U.S. PATENT DOCUMENTS

| | | | |
|---|---|---|---|
| 2,752,918 A | 7/1956 | Uytenbogaart | 128/218 |
| 4,031,893 A | 6/1977 | Kaplan et al. | 128/218 F |
| 4,553,962 A | 11/1985 | Brunet | 604/198 |
| 5,092,842 A * | 3/1992 | Bechtold et al. | 604/135 |
| 5,114,406 A | 5/1992 | Gabriel et al. | 604/136 |
| 5,244,465 A | 9/1993 | Michel | 604/208 |
| 5,478,316 A | 12/1995 | Bitdinger et al. | 604/135 |
| 5,480,387 A * | 1/1996 | Gabriel et al. | 604/134 |
| 5,514,097 A | 5/1996 | Knauer | 604/136 |
| 5,599,309 A * | 2/1997 | Marshall et al. | 604/136 |
| 5,658,259 A | 8/1997 | Pearson et al. | 604/232 |
| 5,779,677 A * | 7/1998 | Frezza | 604/134 |
| 6,221,046 B1 * | 4/2001 | Burroughs et al. | 604/153 |
| 6,280,421 B1 * | 8/2001 | Kirchhofer et al. | 604/218 |

FOREIGN PATENT DOCUMENTS

| | | |
|---|---|---|
| DE | 902 776 C | 1/1954 |
| DE | 27 21 545 C2 | 11/1977 |
| DE | 36 45 245 C2 | 5/1988 |
| DE | 42 223 958 A1 | 1/1993 |
| DE | 195 32 410 A1 | 3/1997 |
| EP | 114 145 A | 7/1984 |
| EP | 373 321 A1 | 6/1990 |
| EP | 666 084 | 8/1995 |
| FR | 505 931 A | 8/1920 |
| FR | 1 014 881 A | 8/1952 |
| WO | WO 95/19194 | 7/1995 |
| WO | WO 96/32974 A | 10/1996 |

* cited by examiner

*Primary Examiner*—Thomas Denion
*Assistant Examiner*—Binh Tran

(57) ABSTRACT

An injection device has a housing (50, 60) and therein a spring for storing energy for an injection operation. The spring (94) impinges, in the proximal direction, upon an ejection member (92) for ejecting injection liquid (16) from a vessel, displaceably arranged in the housing, at whose proximal end an injection needle is attached. Located in the housing is a displacement member (36), displaceable in the longitudinal direction, for displacing the vessel (14) in the proximal direction, in order to effect a movement of the injection needle (18) in the proximal direction and, thus, its insertion. Provided on the ejection member (92) is a detent lug (100), associated with which is a corresponding detent opening (102) in the displacement member (36). A control member (70), effective in travel-dependent fashion, serves to disengage the detent lug (100) from the detent opening (102) when the displacement member (36), during the injection operation, has traveled a predefined distance in the proximal direction.

15 Claims, 10 Drawing Sheets

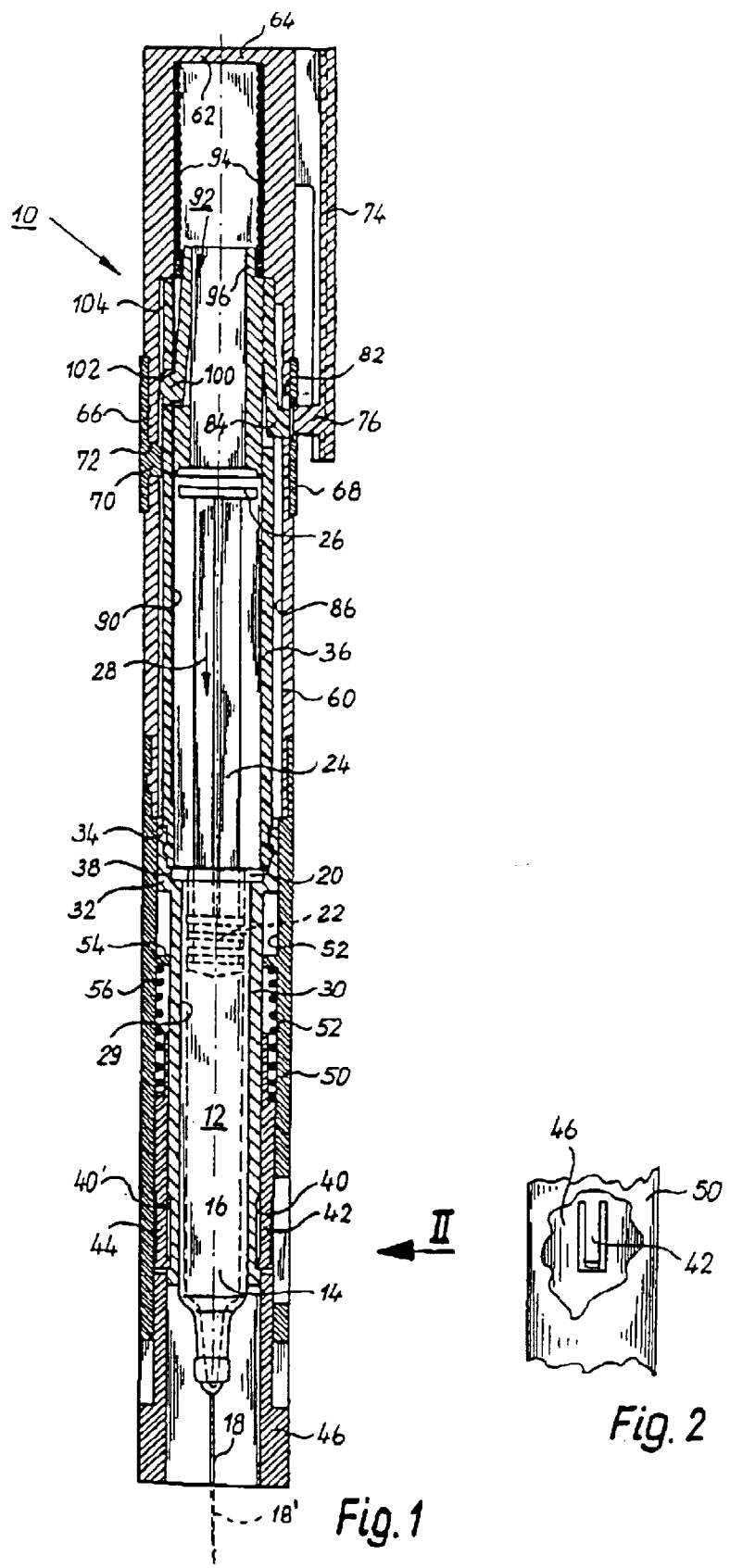

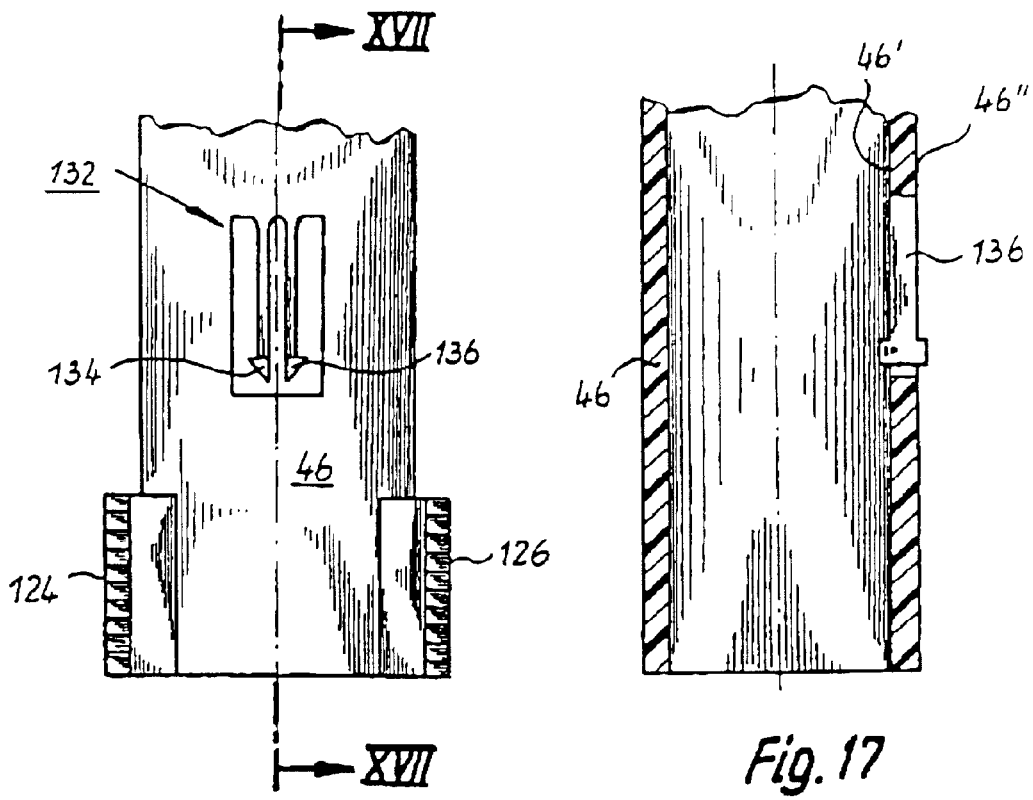
Fig. 16
Fig. 17
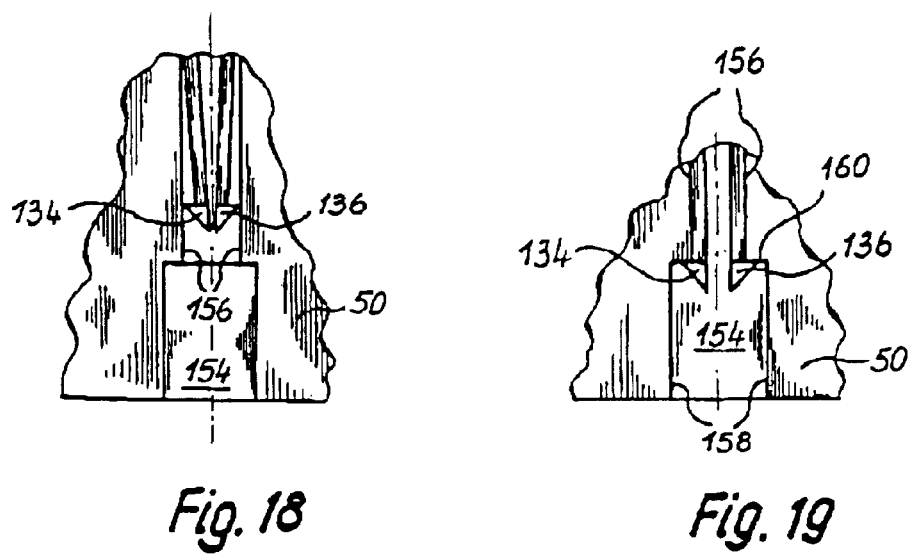
Fig. 18
Fig. 19

INJECTION DEVICE

FIELD OF THE INVENTION

The invention concerns an injection device having a housing and having an energy storage spring for storing energy for an injection operation. This energy serves preferably for automatically inserting an injection needle, and optionally also for automatic injection of an injection liquid. The preferred field of application of the invention is an injection device for one-time use, often also referred to as a disposable syringe.

SUMMARY OF THE INVENTION

It is the object of the invention to make a new injection device available.

According to the invention, this object is achieved by having a control member which disengages a detent lug once a displacement member has traveled a predefined distance in the proximal direction. What is thereby obtained, in simple fashion, is sequential execution of the injection operation, i.e. first the injection needle (hollow needle) is inserted into the patient, and only then, when the needle is already in the subcutaneous fatty tissue, is the active ingredient present in the injection device injected.

Another way of achieving the stated object is to use a spring-loaded needle protection sleeve. Because the proximal and distal end positions of the needle protection sleeve are a function of the position of the vessel container and thus of the displacement member, these end positions can be optimally adapted to requirements before and after an injection.

Further details and advantageous developments of the invention are evident from the exemplary embodiment described below and depicted in the drawings, which is in no way to be understood as a limitation of the invention.

BRIEF FIGURE DESCRIPTION

In the drawings:

FIG. 1 shows an injection device according to the present invention in longitudinal section and in its cocked position, i.e. the position before an injection, and at enlarged scale; in reality, the device depicted in FIG. 1 has, for example, a length of approximately 18 cm and has approximately the shape of an oversized fountain pen;

FIG. 2 is a plan view of the point shown cut away in FIG. 1, view in the direction of arrow II of FIG. 1;

FIG. 16 is a plan view of an arrangement of barbs provided on the needle protection sleeve;

FIG. 17 is a longitudinal section viewed along line XVII—XVII of FIG. 16;

FIG. 18 is a schematic view of the barb arrangement before becoming effective; and FIG. 19 is a schematic view of the barb arrangement after becoming effective.

DETAILED DESCRIPTION OF THE PREFERRED EMBODIMENT

Figure 3:
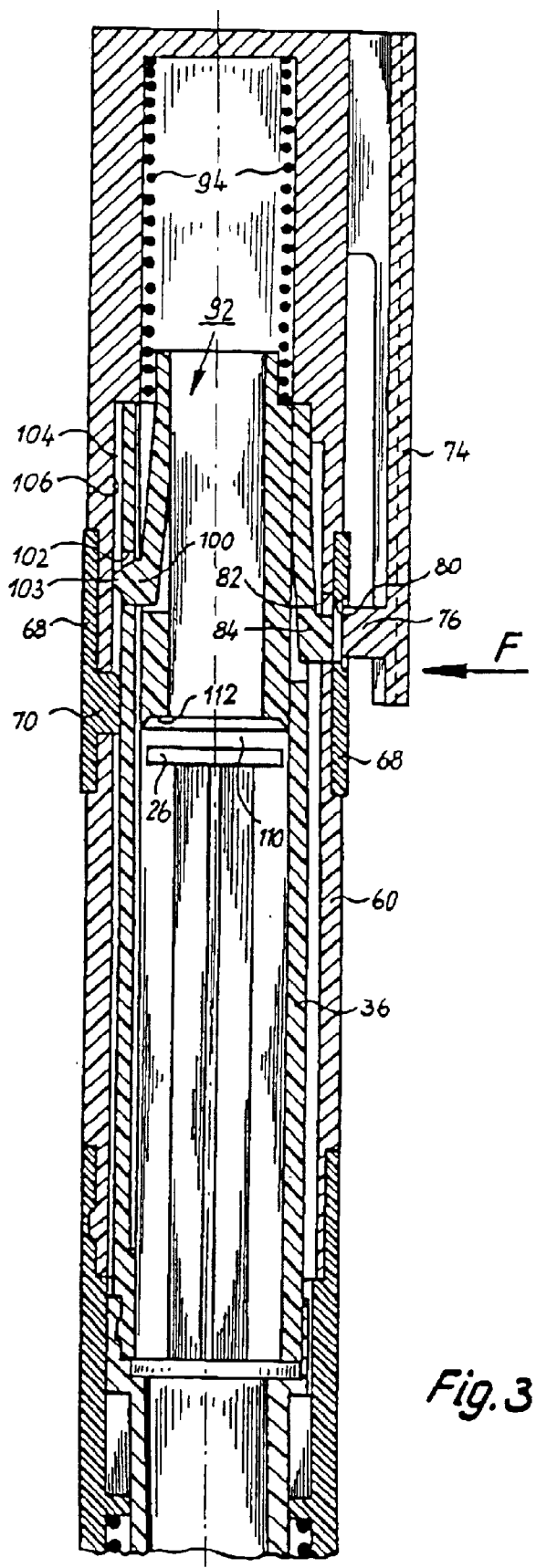
FIG. 3 is a more greatly enlarged depiction of the upper half of the injection device of FIG. 1 with the device in the cocked position, i.e. before an injection operation.

In the description which follows, the terms "proximal" and "distal" are used in the manner usual in medicine, i.e. "proximal"=facing toward the patient (the end of the injection device having injection needle 18), and "distal"=facing away from the patient.

FIG. 1 shows the totality of an injection device 10 in longitudinal section. In the exemplary embodiment, this is an injection device for one-time use, also called an autoinjector, but the invention can also be used in the context of injection devices that allow multiple use. In this embodiment, there is located in the interior of injection device 10 an injection syringe 12 of commercially available design, having a cylindrical portion 14 to receive the injection liquid 16, at whose proximal end an injection needle 18 is attached in the usual fashion.

Cylindrical portion 14 has at the top, in the usual fashion, an enlargement 20 in the form of so-called syringe flanges. Also provided is a piston 22 that is connected to a piston rod 24 that has a pressure plate 26 at its distal end. When pressure is exerted on pressure plate 26 in the direction of arrow 28, liquid 16 is then ejected through needle 18, as is familiar to those skilled in the art.

Cylindrical portion 14 of commercially available syringe 12 is located in the cylindrical recess 29 of a vessel container 30, which can also be referred to as the syringe container and which has at its distal end region a shoulder 32 against whose distal side enlargement 20 rests as depicted. Shoulder 32 transitions into a collar-shaped segment 34 that, as depicted, is firmly connected to a displacement member 36, of substantially cylindrical configuration, which with its proximal end 38 grips syringe flanges 20 so that the latter are firmly connected to displacement member 36 and vessel container 30, and syringe 12 constrainedly follows their movements.

Vessel container 30 has in the proximal end region two grooves or recesses 40, 40' which lie diametrically opposite one another. A needle protection sleeve 46 has two resilient segments 42, 44, each with a radially inwardly protruding projection 42', 44' at its free end. Projection 42' protrudes into groove 40, projection 44' into groove 40'. FIG. 2 shows resilient segment 42 in plan view.

Needle protection sleeve 46 is thus displaceable between a proximal and a distal end position, whose spacing is determined by the (identical length of grooves 40, 40'. As vessel container 30 is displaced in the proximal direction upon injection, the position of grooves 40, 40' also changes, and thus so do the proximal and distal end positions of needle protection sleeve 46 as will be described in detail below, i.e. both end positions are then displaced in the proximal direction. Grooves 40, 40' also effect longitudinal guidance of needle protection sleeve 46.

Needle protection sleeve 46 is slidingly displaceable in cylindrical inner side 52 of a proximal housing portion 50. From cylindrical inner side 52, an annular shoulder 54 protrudes radially inward. This serves an abutment for a compression spring 56 which, as depicted, acts upon needle protection sleeve 46 in the proximal direction, i.e. toward the patient.

Figure 4:
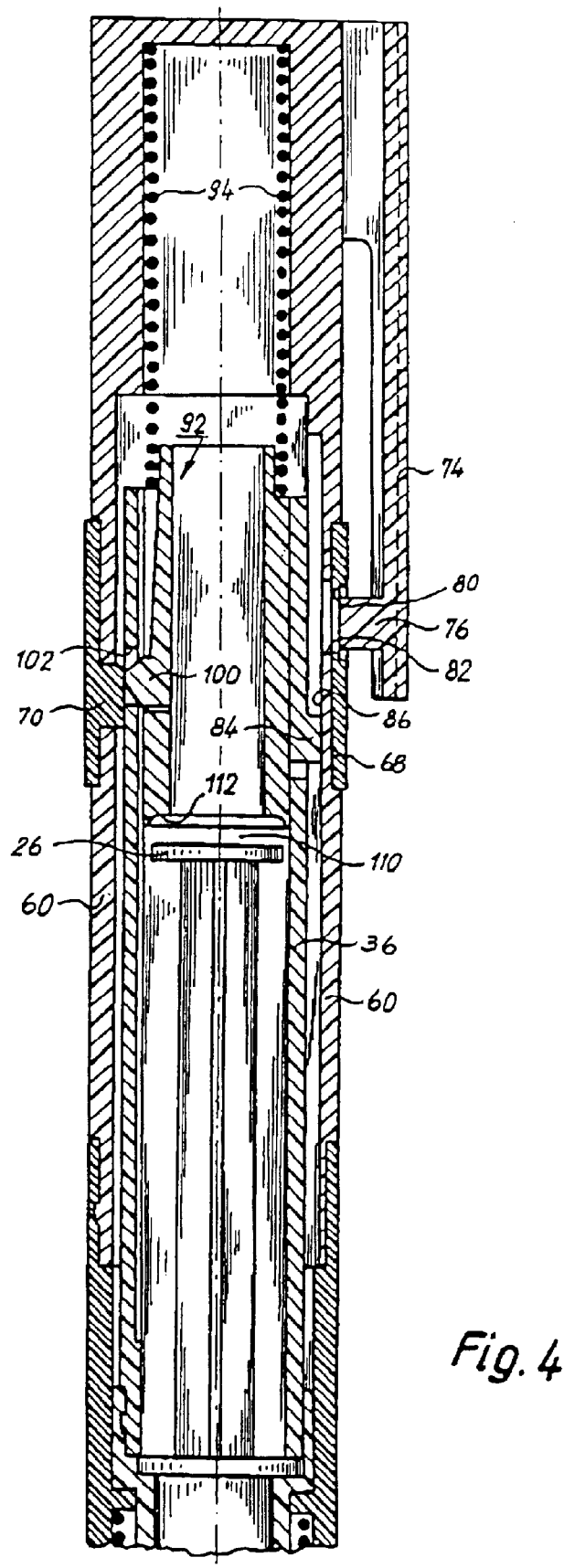
FIG. 4 is a view similar to FIG. 3 but after initiation of an injection operation, although the needle has merely been inserted whereas an injection has not yet taken place.
Figure 5:
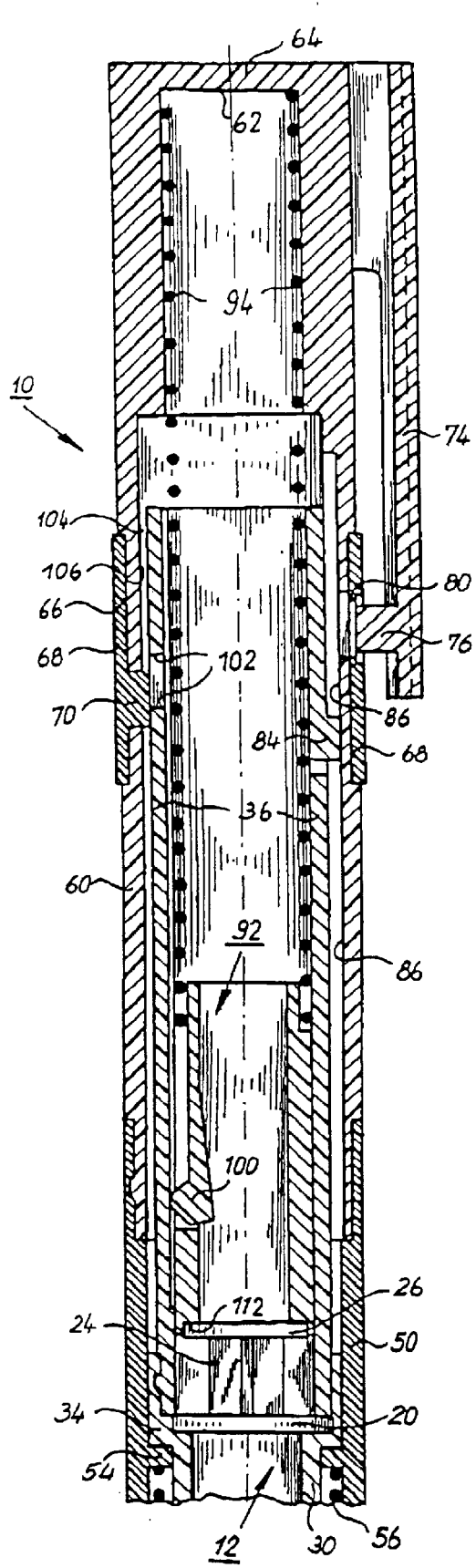
FIG. 5 is a view similar to FIGS. 3 and 4, but after an injection has been completely performed.

Collar-shaped segment 34 is also displaceable in cylindrical inner side 52 as depicted, specifically from its distal end position depicted in FIGS. 1 and 3 to its proximal end position depicted in FIGS. 4 and 5, in which segment 34 is in contact against annular shoulder 54.

Firmly connected to proximal housing portion 50, as depicted, is a distal housing portion 60. The latter has an interior space 62 that is closed off at the top, i.e. at the distal end, by a closure wall 64. Located on the outer side of housing portion 60, in an annular groove 66, is a rotatable annular element 68 that has a control member or cam segment 70 which projects through an opening 72, as depicted, into the interior of distal housing portion 60.

Located on the outer side of distal housing portion 60, as depicted, is a triggering member 74 that has approximately the shape of the retaining clip of a fountain pen. In the region of its unattached (proximal) end, triggering member 74 has a radially inwardly protruding projection 76 which serves to trigger an injection operation. In FIG. 1, this is prevented by annular element 68, which is in its locking position and thus blocks any movement of projection 76 to the left. FIGS. 3 through 5 show this annular element 68 in a rotational position in which it makes possible the triggering of an injection, because there is present therein, opposite projection 76, a recess 80 of annular element 68 which then aligns with a recess 82 of distal housing portion 60.

As FIG. 1 shows, in the cocked state a radially outwardly deflecting detent element 84, which in this case is configured integrally with displacement member 36, snaps into recess 82. Associated with this detent element 84 on the inner side of distal housing portion 60 is a longitudinal groove 86 in which detent element 84 is displaced during the injection operation (cf. FIGS. 4 and 5).

An ejection member 92 is arranged in slidingly displaceable fashion in cylindrical inner side 90 of displacement member 36. It is acted upon in the proximal direction by a compression spring 94 that, in the cocked state (FIGS. 1 and 3), stores the energy necessary for performing an injection operation. As depicted, spring 94 is braced at its distal end against housing segment 64, and at its proximal end against an annular shoulder 96 of ejection member 92.

Figure 6:
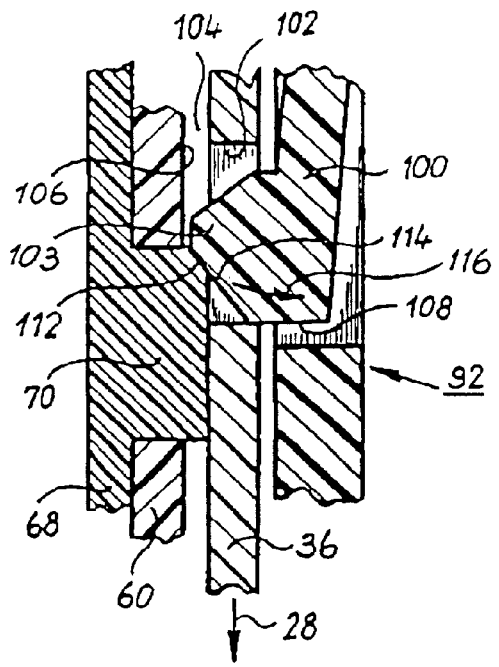
FIGS. 6–8 are schematic depictions to explain the sequential execution of an injection.
Figure 8:
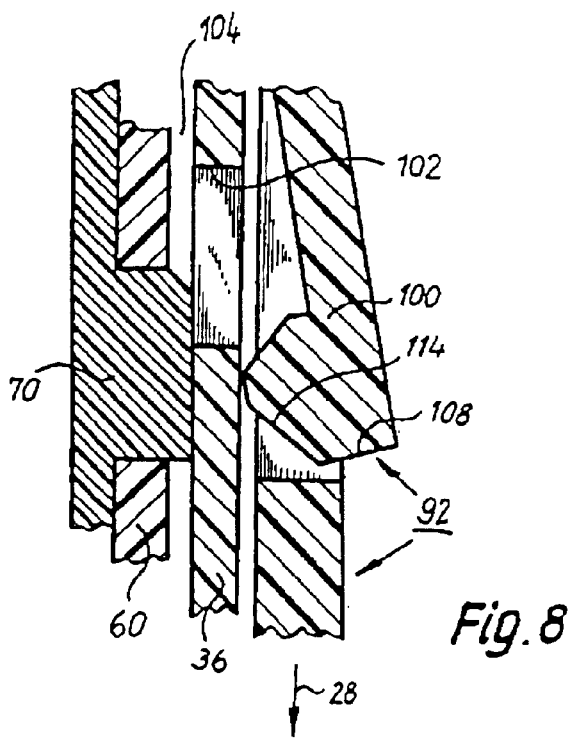
Figure 7:
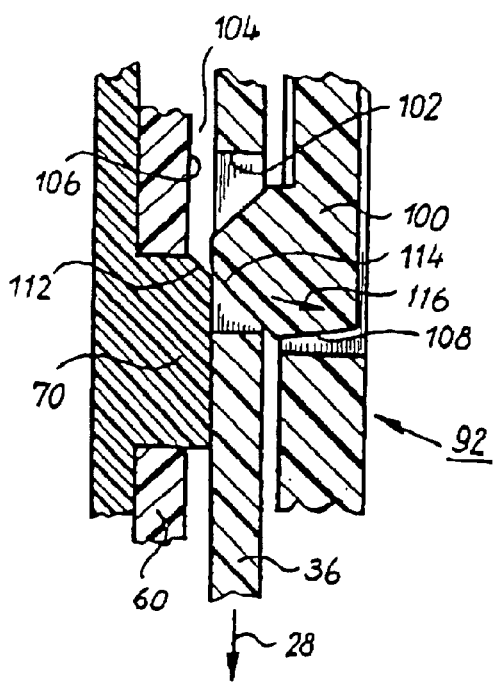

Ejection member 92 is configured integrally with a flexible detent member or lug 100 whose form and function are best evident from FIGS. 6 through 8. When injection device 10 is in the cocked state (FIGS. 1 and 3), detent member 100 projects into a detent opening or recess 102 of displacement member 36, and through this recess 102 it projects with a radial protrusion 103 radially outward into a radial space or gap 104 between displacement member 36 and inner side 106 (FIGS. 6 and 7) of distal housing portion 60. In that context, it is braced at a radially extending surface 108 against a corresponding countersurface of opening or recess 102, as shown in greatly magnified fashion in FIG. 6, so that the force of spring 94 is transferred via detent member or lug 100 to displacement member 36, and acts upon the latter in the proximal direction before an injection begins.

Mode of operation

In order to trigger an injection, in FIG. 3 member 74 is acted upon by a force F and thereby displaces resilient detent member 84 of displacement member 36 radially inward, so that the latter comes out of engagement with recess 82 of distal housing portion 60.

Figure 14:
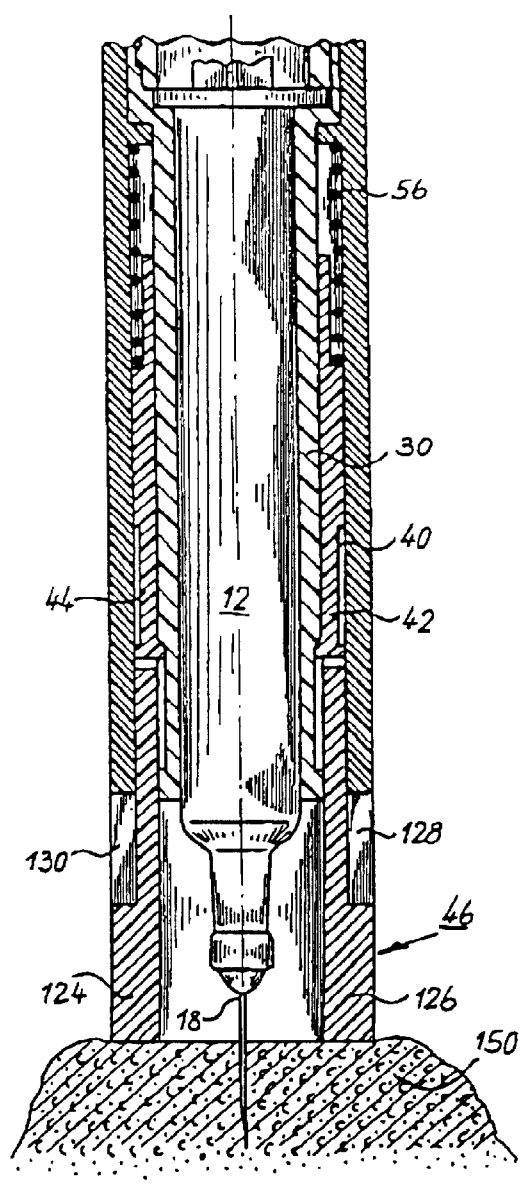
FIG. 14 is a view of the proximal portion of the injector after the needle has been inserted into the subcutaneous fatty tissue of the patient.

As a result, as shown in FIG. 4, ejection member 92 and displacement member 36 can be displaced together in the proximal direction in response to cocked spring 94, since they are coupled to one another by flexible detent member or lug 100, and needle 18 is thus displaced into the position labeled 18' in FIG. 1, thus inserting it into the subcutaneous fatty tissue of the patient (cf. FIG. 14).

As shown in FIG. 4, in this context an axial gap 110 initially remains between proximal end 112 of ejection member 92 and pressure plate 26, since the syringe 12 moves synchronously with displacement member 36 and consequently the positions of these parts relative to one another do not change. The size of gap 110 depends on the magnitude of liquid volume 16 in syringe 12.

When the position shown in FIG. 4 is reached, flexible detent member 100 is deflected radially inward by projection 70 so that it comes out of engagement with recess 102 of displacement member 36.

The manner in which this occurs is shown by FIGS. 6 through 8, which actually require no explanation. Projection 70 has on its distal side an oblique surface that, on radial protrusion 103, corresponds to a complementary oblique surface 114 of flexible detent member or lug 100. When a movement occurs in the direction of arrow 28, oblique surfaces 112 and 114 slide along one another and push flexible detent member 100 radially inward in the direction of an arrow 116, so that (as shown in FIG. 7) it comes out of engagement with the associated recess 102 of displacement member 36 and (as shown in FIG. 8) moves automatically in the proximal direction in response to compression spring 94.

In this context, as shown in FIG. 5, proximal end face 112 of ejection member 92 presses against pressure plate 26 and displaces the latter as far as the stop in the commercially available syringe 12, so that the liquid 16 is ejected from the latter and injected through needle 18 into the patient. FIG. 5 shows the position that is reached after completion of the (automatically proceeding) injection operation.

Figure 9:
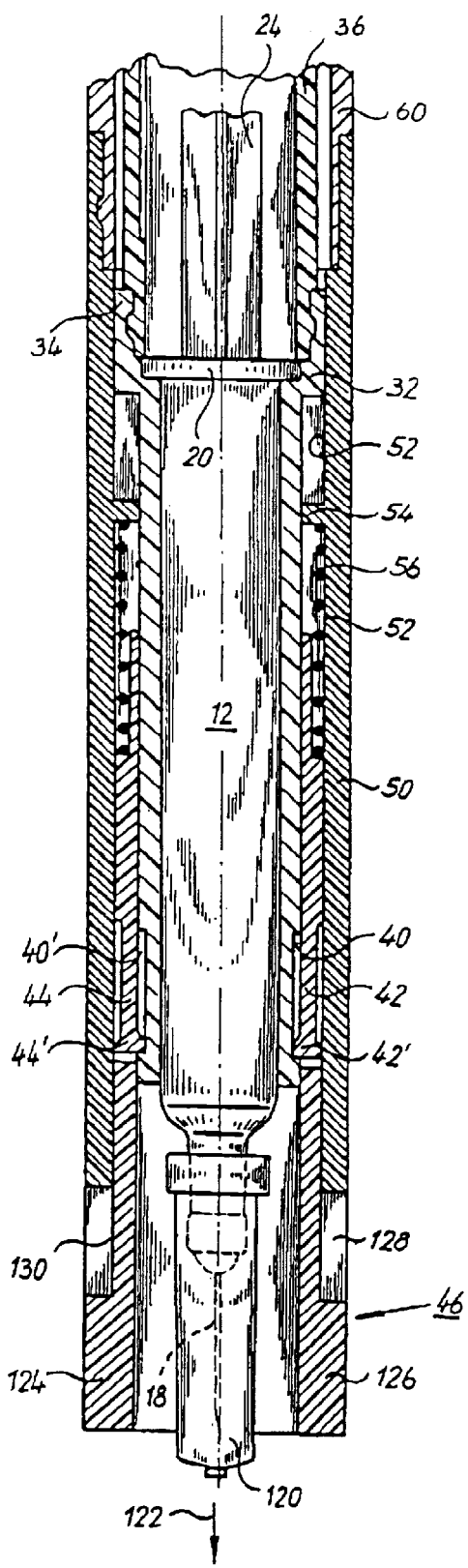
FIG. 9 shows the proximal portion of the injector before removal of the needle cover cap which covers the hollow needle in sterile fashion.

FIG. 9 is largely the same as the depiction of FIG. 1. It shows the manner in which, prior to an injection, a sterile needle cover cap 120 must be pulled off in the direction of an arrow 122 so that the needle can be inserted. In the present case, removal of needle cover cap 120 would be possible only with the aid of a forceps.

For this reason, needle protection sleeve 46 has two radial projections 124, 126 with which it projects into axially extending cutouts 128, 130 of proximal housing portion 50 and is axially displaceable in those cutouts.

Figure 11:
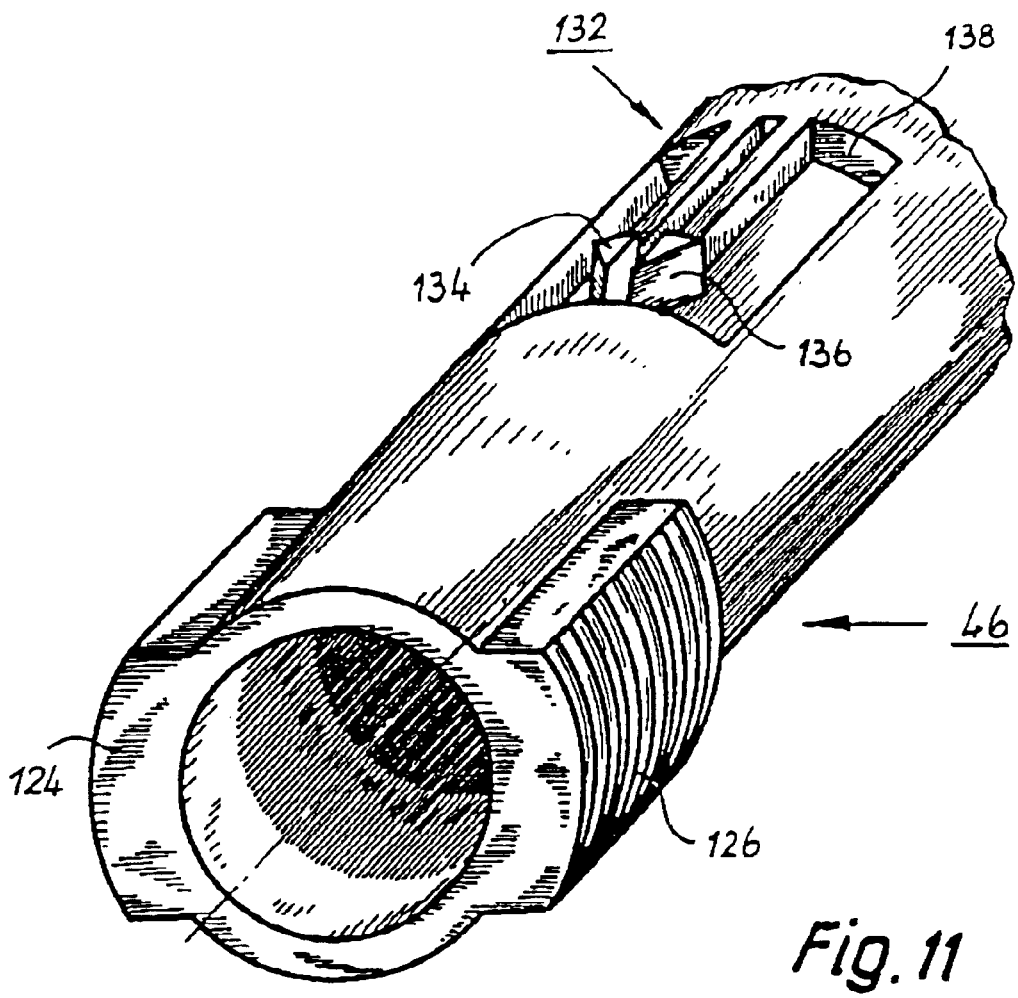
FIG. 11 is a perspective view of the proximal end segment of the needle protection sleeve.

FIG. 11 shows, in a perspective depiction, the proximal portion of needle protection sleeve 46. This also has a detent arrangement 132 having two resilient barbs 134, 136 that are located in a window 138. Arrangement 132 and its function are explained below. As clearly depicted in FIG. 17, barbs 134, 136 project inward and outward radially beyond inner circumference 46' and outer circumference 46'', respectively, of needle protection sleeve 46. The outward protrusion provides guidance in a longitudinal groove 154 of housing portion 50, as depicted in FIGS. 18 and 19. The purpose of the inward protrusion is to deflect barbs 134, 136 toward one another upon assembly (cf. FIG. 18).

Figures 12, 13:
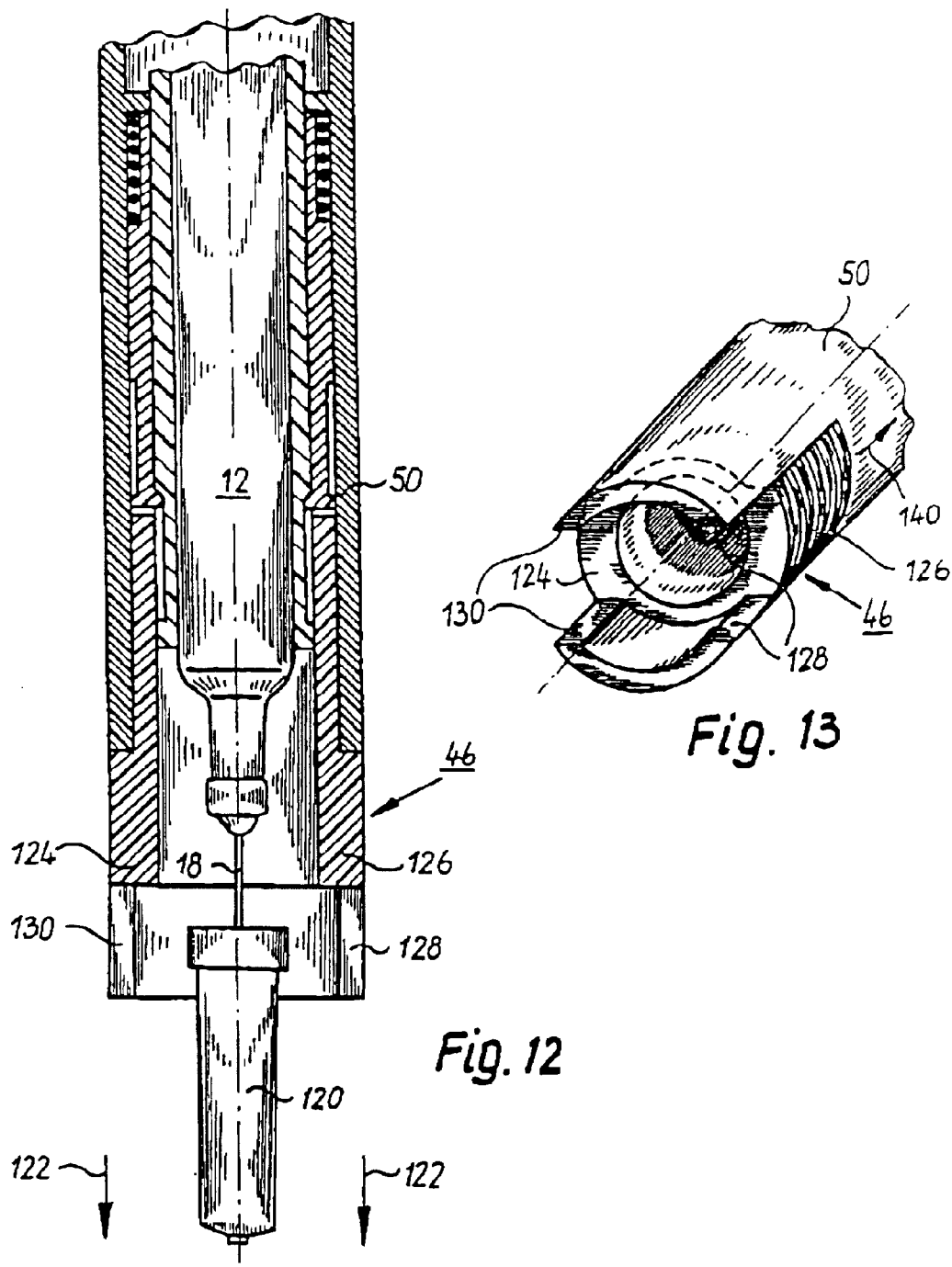
FIG. 12 is a view of the proximal portion of the injector upon removal of the needle cover cap.
FIG. 13 is a perspective view for better comprehension of FIG. 12.

FIGS. 12 and 13 show the manner in which needle protection sleeve 46 has been displaced distally in the direction of an arrow 140 relative to housing 50, so that the patient can now grasp the sterile needle cover cap 120 through recesses 128, 130 and pull it off needle 18 in the direction of arrows 122 in order to prepare for an injection.

FIG. 14 shows needle 18 after it has been inserted into subcutaneous fatty tissue 150 of the patient. This position corresponds to the position depicted in FIG. 4 (before injection of the liquid), and is identical to the position depicted in FIG. 5 (after injection of the liquid). The difference between the two figures is the position of piston 22 in cylinder 14; this piston is not depicted in FIG. 14.

Figure 10:
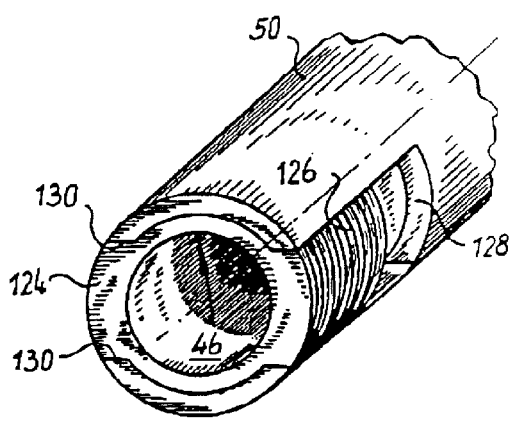
FIG. 10 is a perspective view for better comprehension of FIG. 9.

In FIG. 14, needle protection sleeve 46 once again occupies the position depicted in FIGS. 9 and 10, but its two projections 42', 44' are now located at the upper (i.e. distal) end of grooves 40 and 40', since vessel container 30 has been displaced in the proximal direction upon the insertion of needle 18.

As a result, the distal end position of needle protection sleeve 46 has thus correspondingly changed, as has its proximal end position, which has migrated farther down as compared to FIG. 14.

Figure 15:
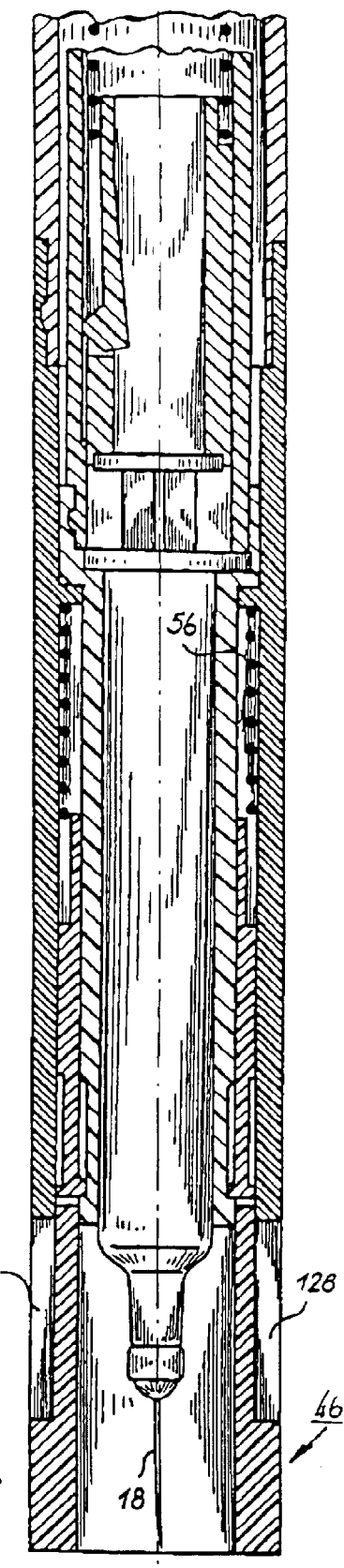
FIG. 15 is a view of the proximal portion of the injector after the needle has been pulled out; the latter is, in this context, completely surrounded by the needle protection sleeve to prevent anyone from being injured by the needle or infected with a disease.

When needle 18 is then pulled out of the subcutaneous fatty tissue as shown in FIG. 15, needle protection sleeve 46 is thus displaced by its compression spring 56 into its new proximal end position, which is depicted in FIG. 15 and in which it completely encloses needle 18 in order to prevent any danger of injury.

In the position shown in FIG. 15, needle protection sleeve 46 is permanently snap-locked in place so that it cannot inadvertently be slid back against the force of compression spring 56, the result of which would be that someone could be injured or infected by needle 18. This is accomplished by way of the two detent hooks 134, 136 of apparatus 132, which is depicted in perspective in FIG. 11. Associated with these detent hooks in housing portion 50 on its inner side is a longitudinal groove 154 which is narrow in its distal region 156 so that detent hooks 134, 136 are compressed there, as depicted in FIG. 18.

As depicted in FIG. 19, when device 10 is in the position shown in FIG. 15, detent hooks 134, 136 arrive in a wider region 158 at the proximal end of groove 154 and thus snap into place at transition point 160. This corresponds to the position of the injector shown in FIG. 15, in which needle protection sleeve 46 is permanently snap-locked into its new proximal end position which has thus also become the (final) distal end position when the injection device, after use, has become waste.

With the exception of springs 56 and 94, the parts of injection device 10 are preferably made of plastic, for example of ABS (acrylonitrile-butadiene-styrene polymer), PC (polycarbonate), or POM (polyoxymethylene).

Preferred materials are:

Housing portions 50, 60, needle protection housing 46, ejection member 92, and displacement member 36: POM or ABS; Vessel container 30: POM or PC.

The selection of plastics is preferably consistent in order to simplify recycling of the injection device.

Many variations and modifications are of course possible in the context of the present invention.

What is claimed is:

1. An injection device comprising
a housing and an energy storage spring arranged therein for storing energy for an injection operation, said housing having an end proximal to a patient and an end distal with respect to said patient,
an ejection member, acted upon in the proximal direction by said energy storage spring, for ejecting injection liquid from a vessel with injection liquid, displaceably arranged in the housing, said vessel having a proximal end adapted for mounting an injection needle;
a displacement member, displaceable in the longitudinal direction in the housing, for displacing the vessel in the housing in the proximal direction in order to effect a movement of the injection needle in the proximal direction and thus, during the injection operation, an insertion of the injection needle;
a detent lug, provided on the ejection member, associated with which is a corresponding detent opening in the displacement member, the detent lug and detent opening together forming a releasable joining member between the ejection member and displacement member; and
a control member, effective in position-dependent fashion, for disengaging the detent lug from the detent opening when the displacement member, during the injection operation, has traveled a predefined distance in the proximal direction,
in order, after disengagement of the detent lug,
to effect a proximal movement of the ejection member independent of a proximal movement of the displacement member, and thus an ejection of injection liquid from the vessel.

2. The injection device as defined in claim 1, wherein the detent lug, in the snapped-in state, projects with a radial protrusion beyond the outer circumference of the displacement member, and by way of an element located in the displacement path of said radial protrusion, is deflectable inward when a proximal movement of the displacement member occurs and thereby is releasable from the detent opening associated with it.

3. The injection device as defined in claim 2, in which the detent lug has on its proximal side, viewed from inside to outside, firstly a substantially radially extending segment for snap-locking with the detent opening associated with it, and adjacent thereto an obliquely extending segment that, proceeding from the radially extending segment, extends obliquely outward in a radial and distal direction.

4. The injection device as defined in claim 1, in which there is provided, between the displacement member and the housing, a releasable first detent connection which, when the energy storage spring is cocked, allows snap-locking of the displacement member in the housing, and which, when released, effects triggering of an injection operation.

5. The injection device as defined in claim 4, in which a locking member for locking the first detent connection is provided in order to make triggering of an injection lockable.

6. The injection device as defined in claim 1, in which the ejection member is arranged in the interior of the displacement member is arranged in the interior of the displacement member and is displaceable relative to the latter in the longitudinal direction of the injection device.

7. An injection device having a housing and a spring arranged therein serving as energy store for the insertion of an injection needle, having a spring acting in the proximal direction on said displacement member, the displacement member being displaceable in the housing between a distal and a proximal end position, and there being associated with it a releasable detent apparatus in order to snap-lock it in its distal end position in which the spring is cocked;

having a vessel container for receiving a vessel having injection liquid, said vessel container being, at its proximal end, connectable to the injection needle, and being joined to the displacement member in such a way that movements of the displacement member in the proximal and in the distal direction are transferred to the vessel container; and having a needle protection sleeve, arranged in the region of the injection needle at the proximal end of the housing, which sleeve is displaceable from a proximal end position, against the force of an associated spring, into a distal end position, the proximal and distal end positions of the needle protection sleeve being a function of the position of the vessel container relative to the housing.

8. The injection device as defined in claim 7, in which the proximal end position of the needle protection sleeve before an injection operation is substantially identical to the distal end position of the needle protection sleeve after an injection operation.

9. The injection device as defined in claim 7, in which there is provided, between the needle protection sleeve and vessel container, a mechanical connection which makes possible a displacement of the needle protection sleeve relative to the vessel container within predefined limits.

10. The injection device as defined in claim 7, in which the needle protection sleeve has a detent arrangement which, in the region of a proximal end position of the needle protection sleeve brought about, after completion of an injection operation, by the spring associated with the needle protection sleeve, effects a snap-lock join with the housing.

11. An injection device comprising a housing and an energy storage spring arranged therein for storing energy for an injection operation, an ejection member, acted upon in the proximal direction by said spring, for ejecting injection liquid from a vessel with injection liquid, displaceably arranged in the housing, said vessel having a proximal end adapted for mounting an injection needle;

a displacement member, displaceable in the longitudinal direction in the housing and joined to the ejection member via a releasable joining member which is firmly connected to the vessel for the injection liquid, for displacing the vessel in the housing in the proximal direction in order to effect a movement of the injection needle in the proximal direction and thus, during the injection operation, an insertion of the injection needle;

a control member, effective in position-dependent fashion, for releasing the releasable joining member when the displacement member, during the injection operation, has traveled a predefined distance in the proximal direction; and a releasable detent connection, which is provided between the displacement member and the housing, allows snap-locking of the displacement member in the housing when the energy storage spring is cocked, and is triggerable by radial pressure on an actuation member, in order, by way of radial pressure on said actuation member, to make possible the triggering of an injection operation in which first the displacement member and ejection member are together driven by the energy storage spring via the joining member in order to effect insertion of the injection needle, and then, after the releasable joining member has been released, injection liquid is ejected from the vessel by the ejection member in response to the energy storage spring.

12. The injection device as defined in claim 11, in which a locking member for locking the releasable detent connection is provided.

13. The injection device as defined in claim 12, in which the locking member is configured to lock a triggering movement of the actuation member.

14. The injection device as defined in claim 12, in which the locking member has a portion that is configured as a position-dependent control member for releasing the releasable joining member.

15. The injection device as defined in claim 13, in which the locking member has a portion that is configured as a position-dependent control member for releasing the releasable joining member.

* * * * *